US012673081B2

(12) United States Patent
Zou et al.

(10) Patent No.: US 12,673,081 B2
(45) Date of Patent: Jul. 7, 2026

(54) TRADITIONAL CHINESE MEDICINE COMPOUND COMPOSITION WITH IMMUNE BIDIRECTIONAL REGULATION EFFECT AND PREPARATION METHOD AND APPLICATIONS THEREOF

(71) Applicants: Chenland Nutritionals Inc., Irvine, CA (US); Qingdao Chenland Biological Technolgy Co., Ltd., Qingdao City (CN)

(72) Inventors: Shengcan Zou, Qingdao (CN); Jiancheng Zong, Qingdao (CN); Haiyan Dong, Qingdao (CN); Weixia Wang, Qingdao (CN); Ning Ding, Qingdao (CN); Lei Zong, Qingdao (CN); Shanglong Wang, Qingdao (CN); Chaoqi Zhao, Qingdao (CN)

(73) Assignees: Qingdao Chenland Health Industry Group Co., Ltd, Qingdao (CN); Chenland Nutritionals, Inc., Irvine, CA (US)

( * ) Notice: Subject to any disclaimer, the term of this patent is extended or adjusted under 35 U.S.C. 154(b) by 824 days.

(21) Appl. No.: 17/529,213

(22) Filed: Nov. 17, 2021

(65) Prior Publication Data

US 2022/0202892 A1 Jun. 30, 2022

Related U.S. Application Data

(63) Continuation of application No. PCT/CN2021/116428, filed on Sep. 3, 2021.

(30) Foreign Application Priority Data

Dec. 31, 2020 (CN) .......................... 202011625476.6
Aug. 28, 2021 (CN) .......................... 202110998897.1

(51) Int. Cl.
A61K 36/538 (2006.01)
A23L 33/00 (2016.01)
A23L 33/105 (2016.01)
A61K 36/284 (2006.01)
A61K 36/481 (2006.01)
A61P 37/04 (2006.01)

(52) U.S. Cl.
CPC .......... *A61K 36/538* (2013.01); *A23L 33/105* (2016.08); *A23L 33/40* (2016.08); *A61K*

*36/284* (2013.01); *A61K 36/481* (2013.01); *A61P 37/04* (2018.01); *A23V 2002/00* (2013.01)

(58) Field of Classification Search
CPC .. A61K 36/538; A61K 36/284; A61K 36/481; A61K 2236/00; A23L 33/105; A23L 33/40; A61P 37/04; A23V 2002/00
See application file for complete search history.

(56) References Cited

U.S. PATENT DOCUMENTS

2015/0140115 A1* 5/2015 Kim ................... A61K 36/9068
424/549

FOREIGN PATENT DOCUMENTS

| CN | 1785391 | A | * | 6/2006 | |
| CN | 103083484 | A | * | 5/2013 | |
| CN | 104971253 | A | * | 10/2015 | |
| CN | 109806325 | A | * | 5/2019 | |
| CN | 116686724 | A | * | 9/2023 | ........... A01K 1/0155 |

OTHER PUBLICATIONS

Machine translation of CN-1785391-A (Year: 2006).*
Machine translation of CN-103083484-A (Year: 2013).*
Machine translation of CN-104971253-A (Year: 2015).*
Zhang D, et al., CN 116686724 A, machine translation, 27 pages. (Year: 2023).*
Chen S-L, CN-109806325-A, machine translation, 15, pages. (Year: 2019).*

* cited by examiner

*Primary Examiner* — Aaron J Kosar

(57) ABSTRACT

A traditional Chinese medicine compound composition with immune bidirectional regulation effect and its preparation method and applications are disclosed. The traditional Chinese medicine compound composition with immune bidirectional regulation effect is prepared by compounding a volatile oil obtained after heating and refluxing of *Schizonepetae herba* and an extract jointly extracted by *Schizonepetae herba* extract residue, *Astragali radix* and *Atractylodes macrocephala* in the disclosure. The traditional Chinese medicine compound composition has no side effects and remarkable effect, and the traditional Chinese medicine compound composition disclosed by the disclosure can be used as a dietary supplement or health food raw material to regulate allergic reaction and low immunity. The traditional Chinese medicine compound composition disclosed by the disclosure is suitable for promotion and application.

9 Claims, 15 Drawing Sheets

TRADITIONAL CHINESE MEDICINE COMPOUND COMPOSITION WITH IMMUNE BIDIRECTIONAL REGULATION EFFECT AND PREPARATION METHOD AND APPLICATIONS THEREOF

CROSS REFERENCE TO RELATED APPLICATION

This patent application is continuation application of PCT/CN2021/116428 filed on Sep. 3, 2021, which further claims the benefits of Chinese Patent Application No. 2020116254766 filed on Dec. 31, 2020 and Chinese Patent Application No. 2021109988971 filed on Aug. 28, 2021, the disclosure of which is incorporated by reference herein in its entirety as part of the present disclosure.

TECHNICAL FIELD

The present disclosure relates to the technical field of natural medicines, in particular to a traditional Chinese medicine compound composition and its preparation method and applications, and more specifically, to a traditional Chinese medicine compound composition with immune bidirectional regulation effect and its preparation method and applications.

BACKGROUND ART

Immune system health is regarded as the second largest health field after intestinal health. A healthy immune system is a powerful defense line to prevent the body from all violations. Once the immune system is defective or dysfunctional, many diseases will come uninvited, ranging from colds, seasonal influenza to cancer. In general, the autoimmune system will turn on the automatic defense mode, but with the burden of aging, lifestyle, work pressure and other aspects, the immune system will be overwhelmed, and pathogens will have an opportunity to take advantage of it. More and more consumers realize that health is also a process that needs maintenance, and immune supplements or functional immune foods are not only suitable for colds or influenza, and more and more immune products are waiting for developers to meet their needs.

The existing immune related products can be divided into two categories: immune products and anti-allergic products. Under the influence and publicity of mainstream consciousness, most people have high enthusiasm in purchasing immune products. However, blindly improving immunity may make the human immune system in an excessively high state. When the immune system capacity of the body is too high, it will be indiscriminate between the enemy and ourselves, attack normal cells in the body, and make the body in a highly sensitive state:

One is that the immune system may overreact to substances outside the body, commonly known as "allergy". At this time, almost all substances can become allergens, such as dust, pollen, drugs or food. As antigens, they stimulate the body to produce abnormal immune response, resulting in allergic rhinitis, allergic asthma, urticaria (rubella mass), allergic conjunctivitis, food allergy, food intolerance, etc.

The other is that the immune system reacts to its own tissue cells in the body, which causes the so-called autoimmune system diseases, the most common including systemic lupus erythematosus, rheumatoid arthritis, ankylosing spondylitis, systemic vasculitis and so on.

Therefore, it is an urgent problem for those skilled in the art to develop a traditional Chinese medicine compound composition with no toxic and side effects, remarkable effect and improving immunity without excessive immunity.

SUMMARY

In view of this, an object of the disclosure is to provide a traditional Chinese medicine compound composition with immune bidirectional regulation effect according to the problems existing in the prior art. The traditional Chinese medicine compound composition has no side effects and remarkable effect, and the traditional Chinese medicine compound composition disclosed by the disclosure can be used as a dietary supplement or health food raw material to regulate allergic reaction and low immunity.

In order to achieve the above object, technical solutions of the present disclosure are specifically described as follows.

In a first aspect, the disclosure provides a traditional Chinese medicine compound composition with immune bidirectional regulation effect. The traditional Chinese medicine compound composition is prepared by compounding a volatile oil obtained after heating and refluxing of *Schizonepetae Herba* and an extract jointly extracted by *Schizonepetae Herba* extract residue, *Astragali radix* and *Atractylodes macrocephala*. And the traditional Chinese medicine includes:

1~100 parts by weight of *Schizonepetae herba*;
1~300 parts of *Astragali radix*; and
1~150 parts of *Atractylodes macrocephala*.

Preferably, the optimal ratio of the *Astragali radix*, *Atractylodes macrocephala* and *Schizonepetae herba* in the traditional Chinese medicine compound composition is 3-5:1-2:1-2.

It should be noted that, the raw materials of the extracts used herein are scientifically selected (from immune bidirectional regulation related prescriptions) and combined organically according to the compatibility of traditional Chinese medicines rather than simple superimposing of the effect of each Chinese medicine. Effects of the abovementioned traditional Chinese medicine materials are listed as follows:

*Schizonepetae herba*

Functions: relieving exterior, dispersing wind, penetrating rash and eliminating sore.

Indications: cold, headache, measles, rubella and sores.

*Astragali radix*

Functions: replenishing Qi and solidifying the surface, supporting toxin, discharging pus, diuresis and generating muscle.

Indications: Qi deficiency and fatigue, long diarrhea and anal prolapse, spontaneous sweating, edema, uterine prolapse, chronic nephritis, proteinuria, diabetes and long-term non-healing of sores.

*Atractylodes macrocephala*

Functions: tonifying Qi, strengthening spleen, drying dampness and benefiting water, calming fetus and stopping diarrhea.

Indications: It is mainly used to treat patients with low immunity caused by weak temper and easy to catch a cold. *Atractylodes macrocephala* is often treated with *Astragali radix*.

Modern pharmacological studies have shown that *Astragali radix* can regulate the innate immune system and activate, stimulate and regulate monocyte macrophages and dendritic cells. It can also regulate the specific immune system and has a wide range of regulatory effects on immune organs, T lymphocytes, B lymphocytes and a variety of cytokines.

*Atractylodes macrocephala* can effectively promote the proliferation of mouse spleen lymphocytes, significantly promote the secretion of cytokines IL-2, IL-4, IL-10, IL-12 and TGF-β1, and the effect on cytokines IL-2 and TGF-β1 gradually increases with the increase of concentration.

*Schizonepetae herba* has the effects of relieving exterior, dispersing wind, dispersing poison and penetrating rash. It is often used in the treatment of cold headache, sore throat and a variety of skin diseases. Modern studies have confirmed that the exterior relieving effect of exterior relieving drugs is closely related to anti-inflammatory effect. Virus belongs to six external evils in traditional Chinese medicine and is one of the main causes of exterior syndrome. Therefore, the pharmacological effects of *Schizonepetae herba* are mainly reflected in anti-inflammatory, anti-virus and anti-allergy.

However, the application of *Astragali radix, Atractylodes macrocephala* and *Schizonepetae herba* to achieve immune bidirectional regulation has not been reported. The disclosure follows the compatibility theory of traditional Chinese medicine and designs an optimized proportion composition with immune bidirectional regulation by combining *Astragali radix, Atractylodes macrocephala* and *Schizonepetae herba*.

In addition, though the common dosage of each traditional Chinese medicine is known in the prior art, the prescription of the disclosure is made for the target disease by organically combining the above medicines, and its medicinal effect is not equivalent to the simple superposition of the effects of these medicines at a commonly-used amount. Actually, it cannot determine the amount of each medicine in the prescription according to their individual commonly-used amount, and the compounding ratio depends on many factors such as the characteristics of the medicinal materials and the compatibility of monarch drugs, ministerial drugs, adjuvant drugs and envoy drugs, and cannot be determined by experimental means such as comparison method and orthogonal test.

In a second aspect, the disclosure provides a preparation method of the traditional Chinese medicine compound composition with immune bidirectional regulation effect, including: compounding a volatile oil obtained after heating and refluxing of *Schizonepetae herba* and an extract jointly extracted by *Schizonepetae herba* extract residue, *Astragali radix* and *Atractylodes macrocephala*. And the preparation method specifically includes:

(1) heating and refluxing of the *Schizonepetae herba* with purified water, then collecting the volatile oil of the *Schizonepetae herba* and embedding it with β-cyclodextrin for standby;

(2) mixing the *Schizonepetae herba* extract residue filtered in step (1) with the *Astragali radix* and the *Atractylodes macrocephala*, adding purified water to continue extraction to obtain filtrates, and then combining the filtrates to obtain a traditional Chinese medicine extract; and (3) mixing the volatile oil obtained in step (1) with the traditional Chinese medicine extract obtained in step (2) evenly to obtain a mixture, then taking a supernatant after concentrating and ethanol precipitating the mixture, and spray drying and sieving the supernatant to obtain the Chinese medicine compound composition with immune bidirectional regulation effect.

Preferably, in step (1), a volume ratio of the *Schizonepetae herba* to purified water is 1: (5~20), a number of heating and refluxing times of the *Schizonepetae herba* is 1~3 times, and an extraction time is 1~3 h.

Preferably, a volume ratio of purified water to a total volume of the *Schizonepetae herba* extract residue, the *Astragali radix* and the *Atractylodes macrocephala* is (6~8): 1, the *Schizonepetae herba* extract residue, the *Astragali radix* and the *Atractylodes macrocephala* are heated and refluxed twice, a first heating and refluxing time is 1~2 h, and a second heating and refluxing time is 0.5~1.5 h.

Preferably, in step (3), a concentration of the ethanol precipitating is 70%, a spray drying temperature is 150~250° C., and a sieving mesh is 60~80 mesh.

Specifically, the preparation method of the above traditional Chinese medicine compound composition comprises the following steps:

subjecting *Schizonepetae herba* to extraction with water in a volume ratio of 1:8 under heating and refluxing for 3 h, extracting the volatile oil by a volatile oil extraction device, collecting and filtrating the volatile oil to obtain a *Schizonepetae herba* extract residue, mixing the residue, *Astragali radix* and *Atractylodes macrocephala*, subjecting the mixture of the residue, *Astragali radix* and *Atractylodes macrocephala* to extraction with water in a volume ratio of 1:8 for 1.5 h for the first time and 1 h for the second time to obtain the filtrates, combining the filtrates followed by concentration and 70% ethanol precipitating, then taking a supernatant, spray drying at 200° C. and sieving with a sieve of 80 mesh to obtain the Chinese medicine compound composition with immune bidirectional regulation effect.

In a third aspect, the disclosure provides an application in preparation of health foods of the traditional Chinese medicine compound composition with immune bidirectional regulation effect.

Further, the traditional Chinese medicine compound composition can be used as a raw material of dietary supplements or health foods to regulate allergic reaction and low immunity, and a dosage form of the traditional Chinese medicine compound composition is capsule, granule or tablet.

According to the above technical scheme, compared with the prior art, the disclosure provides a traditional Chinese medicine compound composition with immune bidirectional regulation effect and its preparation method and applications, and has the following beneficial effects:

1. The disclosure follows the traditional Chinese medicine compatibility theory, innovates the combination of *Schizonepetae herba, Astragali radix* and *Atractylodes macrocephala*, and finally designs a traditional Chinese medicine compound composition with immune bidirectional regulation effect which can be used to regulate allergic reaction and low immunity.

2. The disclosure adopts the process of combining separate extraction and mixed extraction of medicinal materials, which saves the extraction time and extraction cost to the greatest extent, controls the main active substances of medicinal materials, and ensures the stability and effectiveness of products while following the economic principle.

3. The traditional Chinese medicine compound composition disclosed and protected by the disclosure has a good immune bidirectional regulation effect through the pharmacodynamic experiment.

4. In the traditional Chinese medicine prescription disclosed and protected by the disclosure, *Astragali radix* and

*Atractylodes macrocephala* are the homologous raw materials of medicine and food, while *Schizonepetae herba* has a long edible history, has no side effects and is easy to absorb. It can not only be used to treat the problems of low immunity or allergic reaction, but also effectively avoid the problem of immune imbalance caused by excessive immune enhancement.

5. The traditional Chinese medicine compound composition disclosed and protected by the disclosure verifies its efficacy through animal experiments and molecular mechanism experiments, and its good immune bidirectional regulation effect is determined.

6. The traditional Chinese medicine compound composition disclosed and protected by the disclosure has no toxic side effects and remarkable effects, and can be used as a raw material of dietary supplements or health foods to regulate allergic reaction and low immunity. It can be seen that the traditional Chinese medicine compound composition disclosed by the disclosure is suitable for promotion and application.

BRIEF DESCRIPTION OF THE DRAWINGS

In order to explain the embodiments of the present disclosure, the following drawings that need to be used in the description of the embodiments will be briefly introduced. Obviously, the drawings in the following description are only embodiments of the present disclosure. For those of ordinary skill in the art, other drawings can be obtained based on the drawings disclosed without creative work.

DETAILED DESCRIPTION OF THE EMBODIMENTS

Figure 1:
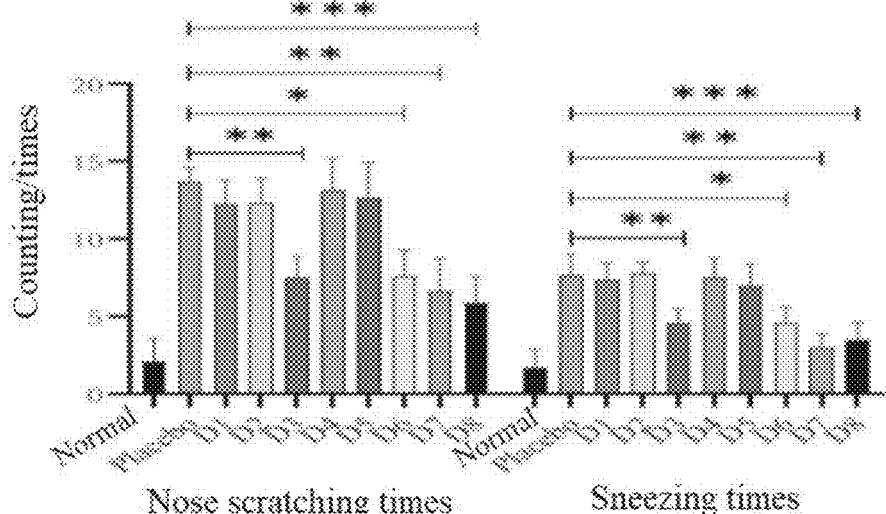
FIG. 1 shows the counting results of nose scratching times and sneezing times of guinea pigs in each group.
Figure 2:
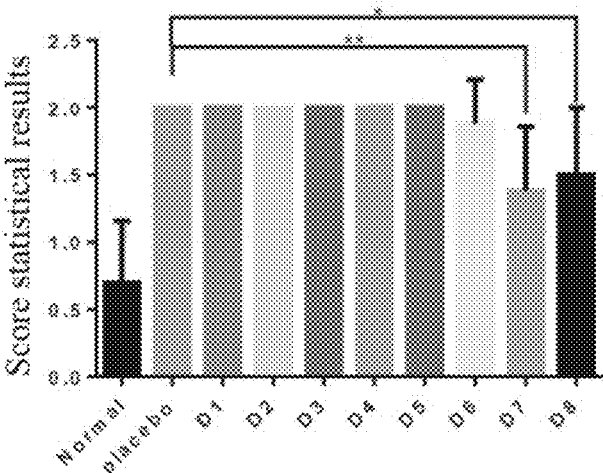
FIG. 2 shows the symptom observation scoring results of guinea pigs in each group.
Figure 3:
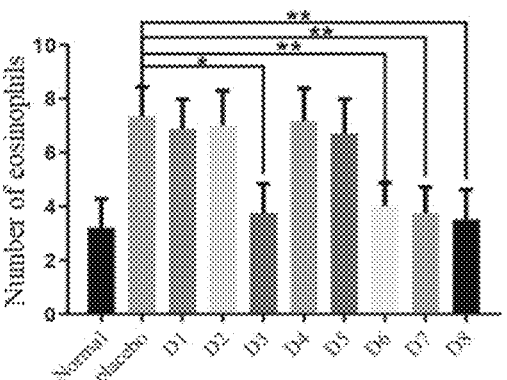
FIG. 3 shows the counting results of eosinophils in nasal lavage solution of guinea pigs in each group.

Technical solutions of the present disclosure will be clearly and completely described below with reference to the embodiments. Obviously, described below are merely some embodiments of the disclosure, which are not intended to limit the disclosure. Other embodiments made by those skilled in the art without sparing any creative effort should fall within the scope of the disclosure.

The embodiments of the disclosure provide a traditional Chinese medicine compound composition with no toxic side effects, easy absorption and remarkable effects. The traditional Chinese medicine compound composition has immune bidirectional regulation effect, and can be used as a raw material of dietary supplement or health foods regulate allergic reaction and low immunity, and thus it is suitable for commercial promotion.

The disclosure will be further described below with reference to the embodiments. It should be understood that these embodiments are merely illustrative of the disclosure, and are not intended to limit the disclosure. Any improvement and modification made by those skilled in the art without departing from the spirit of the disclosure should still fall within the scope of the disclosure.

The technical scheme disclosed by the disclosure will be further described in combination with specific embodiments.

Embodiment 1

A preparation method of the traditional Chinese medicine compound composition with immune bidirectional regulation effect included the following steps:

(1) subjecting *Schizonepetae herba* to extraction with water in a volume ratio of 1:8 under heating and refluxing for 3 h, extracting a volatile oil of the *Schizonepetae herba* with a volatile oil extraction device, collecting the volatile oil and embeding it with $\beta$-cyclodextrin for standby;

(2) mixing the *Schizonepetae herba* extract residue, *Astragali radix* and *Atractylodes macrocephala* according to a dry weight of 1:3:1, adding 8 times the amount of water, and continuing the extraction for 2 times, 1.5 h for the first time and 1 h for the second time; and (3) combining and concentrating the filtrates, adding ethanol until the ethanol content in the solution is 60%, taking the supernatant for concentrating, spray drying the concentrated supernatant at 200° C. and sieving with a sieve of 80 mesh to obtain the traditional Chinese medicine compound composition with immune bidirectional regulation.

Embodiment 2

A preparation method of the traditional Chinese medicine compound composition with immune bidirectional regulation effect included the following steps:

(1) subjecting *Schizonepetae herba* to extraction with water in a volume ratio of 1:8 under heating and refluxing for 3 h, extracting a volatile oil of the *Schizonepetae herba* with a volatile oil extraction device, collecting the volatile oil and embedding it with $\beta$-cyclodextrin for standby;

(2) mixing the *Schizonepetae herba* extract residue, *Astragali radix* and *Atractylodes macrocephala* according to a dry weight of 1:3:1, adding 8 times the amount of water, and continuing the extraction for 2 times, 2 h for the first time and 1.5 h for the second time; and (3) combining and concentrating the filtrates, adding ethanol until the ethanol content in the solution is 70%, taking the supernatant for concentrating, spray drying the concentrated supernatant at 200° C. and sieving with a sieve of 80 mesh to obtain the traditional Chinese medicine compound composition with immune bidirectional regulation.

Embodiment 3: Capsule Preparation

A preparation method of the traditional Chinese medicine compound composition with immune bidirectional regulation effect included the following steps:

(1) subjecting *Schizonepetae herba* to extraction with water in a volume ratio of 1:8 under heating and refluxing for 3 h, extracting a volatile oil of the *Schizonepetae herba* with a volatile oil extraction device, collecting the volatile oil and embedding it with β-cyclodextrin for standby;

(2) mixing the *Schizonepetae herba* extract residue, *Astragali radix* and *Atractylodes macrocephala* according to a dry weight of 1:3:1, adding 8 times the amount of water, and continuing the extraction for 2 times, 2 h for the first time and 1.5 h for the second time; and (3) combining and concentrating the filtrates, adding ethanol until the ethanol content in the solution is 70%, taking the supernatant for concentrating, spray drying the concentrated supernatant at 200° C. and sieving with a sieve of 80 mesh to obtain the traditional Chinese medicine compound composition with immune bidirectional regulation.

The pregelatinized starch, talc powder and magnesium stearate were added to the above prepared traditional Chinese medicine compound composition, mixed evenly, loaded into capsules to prepare capsules.

Embodiment 4: Tablet Preparation

A preparation method of the traditional Chinese medicine compound composition with immune bidirectional regulation effect included the following steps:

(1) subjecting *Schizonepetae herba* to extraction with water in a volume ratio of 1:8 under heating and refluxing for 3 h, extracting a volatile oil of the *Schizonepetae herba* with a volatile oil extraction device, collecting the volatile oil and embedding it with β-cyclodextrin for standby;

(2) mixing the *Schizonepetae herba* extract residue, *Astragali radix* and *Atractylodes macrocephala* according to a dry weight of 1:3:1, adding 8 times the amount of water, and continuing the extraction for 2 times, 2 h for the first time and 1.5 h for the second time; and (3) combining and concentrating the filtrates, adding ethanol until the ethanol content in the solution is 70%, taking the supernatant for concentrating, spray drying the concentrated supernatant at 200° C. and sieving with a sieve of 80 mesh to obtain the traditional Chinese medicine compound composition with immune bidirectional regulation.

The starch and magnesium stearate were added into the prepared traditional Chinese medicine compound composition, mixed evenly, pressed into tablets, coated with film, and made into tablets.

Embodiment 5: Granule Preparation

A preparation method of the traditional Chinese medicine compound composition with immune bidirectional regulation effect included the following steps:

(1) subjecting *Schizonepetae herba* to extraction with water in a volume ratio of 1:8 under heating and refluxing for 3 h, extracting a volatile oil of the *Schizonepetae herba* with a volatile oil extraction device, collecting the volatile oil and embedding it with β-cyclodextrin for standby;

(2) mixing the *Schizonepetae herba* extract residue, *Astragali radix* and *Atractylodes macrocephala* according to a dry weight of 1:3:1, adding 8 times the amount of water, and continuing the extraction for 2 times, 2 h for the first time and 1.5 h for the second time; and (3) combining and concentrating the filtrates, adding ethanol until the ethanol content in the solution is 70%, taking the supernatant to concentrate and decoct to 1 g/mL to obtain an extractum.

The decocted extractum was put into a beaker, to which the weighed sodium lactate monohydrate was introduced, and then the extractum and sodium lactate monohydrate were mixed uniformly to produce a mixture. When the mixture was kneaded into a dough and dispersed when touched, granules that can not pass through the 20-mesh sieve and 80-mesh sieve but can pass the 10-mesh sieve were collected and dried in an oven in time for use.

Then, the prepared granules were put into a vacuum dryer for drying, so that the water content of the granules was controlled at 4%, and the compound granules with immune bidirectional regulation effect were prepared.

Further, the following experiments were performed to evaluate the efficacy of the traditional Chinese medicine compound composition prepared herein.

1. Allergic Rhinitis Experiment

Experimental Animal 100 6-week-old clean guinea pigs, half male and half female, were provided by Qinglongshan animal breeding center, license No. SCXK (SU) 2017-0001. Guinea pigs were fed with special pellet feed (Jiangsu synergy biology Co,, Ltd.) and kept in a clean animal room. 12 h/12 h light/dark cycle, free feeding and drinking, temperature 20-26° C., relative humidity 40-70%.

Experimental Animal Grouping 100 guinea pigs were divided into 20 cages with 5 guinea pigs in each cage. After 7 days of adaptive growth without abnormalities, 90 guinea pigs were used for the construction and induction of allergic rhinitis model, and the remaining 10 guinea pigs were used for normal control. During the whole experiment, the animals were looked after and treated in strict accordance with the animal ethics law.

1.1 Construction of Guinea Pig Model with Allergic Rhinitis

According to the methods described in the preparation and application of medical experimental animal models, the animal center allergic rhinitis model was established, the standard operating procedures were given ovalbumin (OVA) induced stimulation, and the guinea pigs in the normal control group were given the same amount of blank solvent. The specific steps were as follows:

1.1.1 Systemic Basic Sensitization

1) Preparing allergen. 3 g OVA and 3 g aluminum hydroxide powder were weighed, 100 ml of 0.9% sodium chloride solution was added, and the suspension was prepared by ultrasonic oscillation, and it was prepared only when in use.

2) The guinea pigs in the model construction group were intraperitoneally injected with 1 ml of OVA aluminum hydroxide suspension once every other day, a total of 7 times.

3) The guinea pigs in the normal control group were intraperitoneally injected with 1 ml of 0.9% sodium chloride 3) 0.1 ml of 0.9% sodium chloride solution was dropped on each side of each guinea pig in the normal control group. The method and times were the same as those in the model control group.

On the day of modeling, drugs were given by gavage. The gavage concentration of guinea pigs in each group is shown in the table below. Each guinea pig was given once a day, and the Placebo group was given equal volume of drug solution every day for 4 weeks, i.e. 28 days.

TABLE 1

| Grouping and dosage | | | |
|---|---|---|---|
| Group | Label | Preset administration dosage | Concentration |
| Normal | Normal | / | / |
| Negative control | Placebo | / | Equal solvent |
| Competitive products on the market 1 | D1 | 41 mg/kg | 10 mg/ml |
| Competitive products on the market 2 | D2 | 45 mg/kg | 10 mg/ml |
| Laboratory sample 1 | D3 | 116 mg/kg | 30 mg/ml |
| Compound of *Astragali Radix* and *Atractylodes Macrocephala* | D4 | 116 mg/kg | 30 mg/ml |
| Low dose of compound of *Astragali Radix*, *Atractylodes Macrocephala* and *Schizonepetae Herba* | D5 | 58 mg/kg | 15 mg/ml |
| Middle dose of compound of *Astragali Radix*, *Atractylodes Macrocephala* and *Schizonepetae Herba* | D6 | 116 mg/kg | 30 mg/ml |
| High dose of compound of *Astragali Radix*, *Atractylodes Macrocephala* and *Schizonepetae Herba* | D7 | 233 mg/kg | 60 mg/ml |
| Positive drug - Loratadine | D8 | 16 mg/kg | 5 mg/ml | solution. The method and times were the same as those in the model control group.

1.1.2 Enhanced Sensitization

1) Prepare allergen. 1 g OVA was weighed, 200 ml of 0.9% sodium chloride solution was added, and the allergen was prepared by ultrasonic oscillation, and it was prepared only when in use.

2) The prepared 0.5% OVA normal saline solution was placed in the atomizing cup of the ultrasonic atomizer to regulate the flow rate of atomization, about 0.2 ml/min.

3) The guinea pigs in the model construction group were placed in the atomizer for 10 minutes. Each guinea pig inhaled about 2 ml of atomization volume once a day for 4 consecutive times.

4) The guinea pigs in the normal control group inhaled 2 ml of 0.9% sodium chloride solution by atomization, and the method and times were the same as those in the model control group.

1.2 Administration Intervention

1.2.1 Nasal Instillation

1) Prepare allergen. 400 mg of OVA was weighed, 200 ml of 0.9% sodium chloride solution was added, and the allergen was prepared by ultrasonic oscillation, and it was prepared only when in use.

2) 3 days after atomization sensitization, nasal drip with 2% OVA normal saline solution was performed, with 0.1 ml on each side of each guinea pig, once a day for 4 consecutive times.

1.3 General Observation of Guinea Pigs

It was evaluated by scoring on the second day of the last administration, and observed for 30 minutes after nasal instillation. The number of sneezes, the nose scratching degree and nasal secretions were recorded. The scoring criteria are shown in the table below.

TABLE 2

| symptom scoring criteria | | | |
|---|---|---|---|
| Symptom score/ score | Number of sneezes/piece | Degree of nasal scratching | Nasal secretions |
| 1 | 1-3 | Mild | Flowing to anterior nostril |
| 2 | 4-10 | Frequent nose scratching | Beyond the anterior nostril |
| 3 | 10+ | Continual nose scratching | A runny face |

1.4 Final Guinea Pig Plasma Collection

1) After scoring on the second day after the last administration, guinea pigs were anesthetized by intraperitoneal injection of 10% chloral hydrate with the anesthetic dosage of 0.35 ml/100 g;

2) The abdominal cavity was opened, and a 5 ml sterile syringe was inserted into the abdominal vein of the guinea pig, and the venous blood was drawn;

3) The drawn venous blood was put into a heparin tube, mixed well, and left in a chromatography freezer at 4° C. overnight.

4) After centrifugation at 14000 rpm at 4° C. for 15 minutes, the supernatant was taken and stored at −80° C. for use.

1.5 Collection of Final Nasal Lavage Solution

1) After scoring on the second day after the last administration, guinea pigs were anesthetized by intraperitoneal injection of 10% chloral hydrate with the anesthetic dosage of 0.35 ml/100 g;

2) The guinea pig was fixed in a supine and low head position, the normal saline was slowly dropped into one nasal cavity at the rate of 1 ml/min, and the contralateral nasal cavity was continuously pumped with low negative pressure;

3) A small amount of the recovered lavage solution was taken immediately and put into a leukocyte counting plate to count the total number of leukocytes;

4) The remaining lavage solution was added with EDTA (7.7 mol/l) and centrifuged at 14000 rpm at 4° C. for 15 minutes. And the supernatant was stored at −80° C. for use.

1.6 The expression levels of cytokines in guinea pig serum and nasal lavage solution were detected by ELISA. The final serum and nasal lavage solution were taken for the determination of histamine, IgE, IL-4, IFN-γ, thromboxane B2 and leukotriene.

The measurement steps included:

1) taking out the ELISA kit from the refrigerator and balancing it at room temperature for 20 min;

2) setting up blank, standard and sample wells to be tested respectively, where the blank wells do not add samples and enzyme labeling reagents, and during sampling, adding samples to the bottom of enzyme labeling plate, gently shaking and mixing the liquid in the enzyme labeling wells;

3) after sealing the film with a film sealing plate, placing it in a 37° C. incubator for incubation for 30 min;

4) discarding the liquid in the wells, gently spin drying it, and adding 50 μL biotin labeled antibody working solution to each well, and incubating in a 37° C. incubator for 30 min;

5) carefully removing the sealing film, pouring out the liquid in the wells, gently spin drying it, adding washing liquid into each well, standing at room temperature for 30 seconds and then pouring it out, repeating this operation for 5 times and gently patting it dry;

6) adding 50 μL horseradish peroxidase labeled avidin working solution to each well, and incubating in a 37° C. incubator for 30 min;

7) pouring out the liquid in the wells, gently spin drying it, adding washing liquid into each well, standing at room temperature for 30 seconds and then pouring it out, repeating this operation for 5 times and gently patting it dry; and 8) adding 100 μL color developing solution to each well in turn, and developing color in a 37° C. incubator without light for 1.5 min;

9) adding 50 L termination solution to each well to terminate the reaction, then zeroing the blank wells and measure the absorbance (OD value) of each well at 450 nm wavelength, where the determination shall be carried out within 15 min after the termination solution is added.

1.7 Tissue Sampling and Pathological Staining of Guinea Pigs

1) After scoring on the second day after the last administration, guinea pigs were anesthetized by intraperitoneal injection of 10% chloral hydrate with the anesthetic dosage of 0.35 ml/100 g;

2) After peeling off the nasal skin, the maxilla together with the nasal cavity were removed, and the bilateral nasal cavities were completely separated from the middle incisors;

3) The nasal mucosa was carefully removed and fixed with 4% paraformaldehyde for HE staining;

4) All the HE stained pathological sections were observed under the light microscope. The histopathological scoring criteria of guinea pig nasal mucosa are shown in the table below:

TABLE 3

| Histopathological scoring criteria of guinea pig nasal mucosa | |
| --- | --- |
| Symptom | Scoring |
| The epithelial structure of nasal mucosa is complete, arranged neatly, the cilia are of the same thickness, no abnormality is found in blood vessels, no proliferation is found in glands, and there is basically no eosinophil infiltration. | 0 |
| The epithelial structure of nasal mucosa is basically intact, blood vessels are slightly dilated, glands are slightly proliferated, and a small number of eosinophils are infiltrated. | 1 |
| The nasal mucosa is partially exfoliated, the blood vessels are obviously dilated and congested, the glands are obviously proliferated, and more eosinophils are infiltrated. | 2 |
| The epithelial structure of nasal mucosa falls off obviously, the blood vessels are seriously dilated and congested, the glands are seriously proliferated, and a large number of eosinophils are infiltrated. | 3 |

1.7.1 Preparation of Mucosal Tissue Sections

The mucosal tissues fixed in 4% glutaraldehyde solution were taken out and made into 5 μm thick paraffin sections for HE staining.

1.7.1.1 Paraffin Embedding 1) 60%, 70%, 80% and 90% gradient ethanol of the fixed sample were used to dehydrate for 8 h respectively;

2) 100% ethanol I and II were used to dehydrated for 1 h respectively;

3) The xylene I and II were used to make the specimens transparent for 15 min respectively;

4) The specimens were soaked in liquid paraffin and placed in a 65° C. oven for 2 h;

5) The soaked paraffin specimens were taken out and embedded in paraffin;

6) The paraffin was cut into 5 μm thick sections and subjected to HE staining.

1.7.1.2 HE Staining

1) Xylene I and II for 15 min respectively;

2) Gradient ethanol hydration to distilled water;

3) Hematoxylin staining for 5 min;

4) Differentiation with 1% hydrochloric acid and ethanol for 1 min;

5) Tap water anti blue for 30 min;

6) 1 min after eosin staining, washing with tap water for 1 min

7) Gradient ethanol dehydration, xylene I and II for 15 min respectively

8) Gum sealing;

9) Observing and taking photos under the microscope.

1.8 Data Analysis

SPSS 22.0 statistical software was used for data analysis. The results in this evaluation process were expressed in the form of mean+standard error (x+SEM). Independent sample t-test was used for the comparison between the two groups, one-way ANOVA was used for the comparison of differences between multiple groups, the least significant difference method was used for pairwise comparison when the variance was homogeneous, and the rank sum test was used when the variance was uneven, $p<0.05$ means significant difference, and $p<0.01$ means extremely significant difference. Oligo 8.0 was used for mapping.

Result

1.9 General State Observation of Guinea Pigs in Each Group after Administration

TABLE 4

Number and time points of deaths in each group during the experiment

| Group | Number in group | Number after basic sensitization | Number after enhanced sensitization | Number after nasal instillation | Final number |
|---|---|---|---|---|---|
| Normal | 10 | 10 | 10 | 10 | 10 |
| Placebo | 10 | 7 | 7 | 6 | 6 |
| D1 | 10 | 9 | 8 | 7 | 7 |
| D2 | 10 | 9 | 7 | 7 | 6 |
| D3 | 10 | 8 | 8 | 8 | 8 |
| D4 | 10 | 7 | 7 | 6 | 6 |
| D5 | 10 | 8 | 7 | 7 | 7 |
| D6 | 10 | 8 | 8 | 8 | 8 |
| D7 | 10 | 9 | 9 | 8 | 8 |
| D8 | 10 | 9 | 8 | 8 | 8 | sneezing, but still had runny nose. The normal control group only had mild nose scratching symptoms after nasal drip of normal saline, but there were no obvious nose scratching and sneezing symptoms in the second and third 10 minutes.

The number and time points of deaths of each group during the experiment are shown in Table 4. The guinea pigs in the normal control group showed normal performance, with close fitting coat, white luster, agile activity, more food intake and granular stool. The guinea pigs in the model construction group had loose coat, reduced coat luster, less activity and dullness, and decreased food intake.

TABLE 5

Final counting results of nose scratching times and sneezing times of guinea pigs in each group

| Group Symptom | Nose scratching times | Sneezing times |
|---|---|---|
| Normal | 2.10 ± 1.51 | 1.70 ± 1.19 |
| Placebo | 13.67 ± 0.94 | 7.67 ± 1.37 |
| D1 | 12.29 ± 1.48 | 7.43 ± 1.05 |
| D2 | 12.33 ± 1.60 | 7.83 ± 0.69 |
| D3 | 7.50 ± 1.41** | 4.63 ± 0.86** |
| D4 | 13.17 ± 2.03 | 7.50 ± 1.26 |
| D5 | 12.71 ± 2.25 | 7.00 ± 1.41 |
| D6 | 7.63 ± 1.65* | 4.63 ± 0.99* |
| D7 | 6.63 ± 2.12** | 3.00 ± 0.87** |
| D8 | 5.88 ± 1.69*** | 3.50 ± 1.12*** |

(*$p < 0.05$, compared with placebo, **$p < 0.01$, compared with placebo)

TABLE 6

Final scoring results of guinea pig symptom observation in each group

| Group | Normal | placebo | D1 | D2 | D3 |
|---|---|---|---|---|---|
| Scoring | 0.70 ± 0.46 | 2.00 ± 0.00 | 2.00 ± 0.00 | 2.00 ± 0.00 | 2.00 ± 0.00 |

| Group | D4 | D5 | D6 | D7 | D8 |
|---|---|---|---|---|---|
| Scoring | 2.00 ± 0.00 | 2.00 ± 0.00 | 1.88 ± 0.33 | 1.38 ± 0.48** | 1.50 ± 0.50* |

(*$p < 0.05$, compared with placebo, **$p < 0.01$, compared with placebo)

2.0 Comparison Results of Sneezing and Nose Scratching Times of Guinea Pigs in Each Group after Administration Guinea pigs were immunized by intraperitoneal injection of ova and atomized ova. The allergic symptoms were nose scratching, sneezing and runny nose. The guinea pigs with serious reaction had dyspnea, cyanosis of lips, convulsions and even death. The dead autopsy showed atelectasis of guinea pigs. In the first 10 minutes of ova nasal drip attack, guinea pigs in the model group and the treatment group had obvious symptoms such as nose scratching, sneezing and accelerated breathing, but the difference was not significant. In the second 10 minutes, the number of nose scratching and sneezing decreased significantly, but there were runny nose symptoms; In the third 10 minutes, all guinea pigs in each group had no obvious symptoms of nose scratching and Compared with the blank control group, the sneezing times and nose scratching times of guinea pigs in the model group were significantly increased ($p<0.01$). After administration, compared with the model group, the results of each group were analyzed, as follows:

Compared with the nose scratching times in the model group, the nose scratching times in D1 group decreased by 10.1%, D2 group decreased by 9.8%, D3 group decreased by 45.1%, D4 group decreased by 3.7%, D5 group decreased by 7.1%, D6 group decreased by 44.2%, D7 group decreased by 51.5%, and D8 group decreased by 57.0%.

Compared with the model group, the sneeze times in D1 group decreased by 3.1%, D2 group decreased by −2.1%, D3 decreased by 39.6%, D4 group decreased by 2.2%, D5 group decreased by 8.7%, D6 group decreased by 39.6%, D7 group decreased by 60.9%, and D8 group decreased by 54.4%.

Comprehensive comparison showed that D8 group was the best, followed by D7 group, D3 group and D6 group.

2.1 Counting Results of Eosinophils in Nasal Lavage Solution of Guinea Pigs after Administration in Each Group

TABLE 7

| Final counting results of eosinophils in nasal lavage solution of guinea pigs in each group | | | | | |
|---|---|---|---|---|---|
| Group | Normal | Placebo | D1 | D2 | D3 | D4 |
| Number of eosinophils (PCs./ml) | 3.20 ± 1.08 | 7.33 ± 1.11 | 6.86 ± 1.12 | 7.00 ± 1.29 | 3.75 ± 1.09* | 7.17 ± 1.21 |

| | Group | D5 | D6 | D7 | D8 |
|---|---|---|---|---|---|
| | Number of eosinophils (PCs./ml) | 6.71 ± 1.28 | 4.00 ± 0.87** | 3.75 ± 0.97** | 3.50 ± 1.12 |

(*$p < 0.05$, compared with placebo, **$p < 0.01$, compared with placebo)

2.2 Test Results of Final Plasma Cytokines of Guinea Pigs in Each Group

Compared with the blank control group, the number of eosinophils in nasal lavage solution of guinea pigs in the model group increased significantly ($p<0.01$). After administration, compared with the model group, the number of eosinophils in nasal lavage solution of D8 group decreased significantly ($p<0.01$), followed by D7 group, D3 group and D6 group. Compared with the number of eosinophils in nasal lavage solution of the model group, the number of eosinophils in nasal lavage solution in D1 group decreased by 6.4%, D2 group decreased by 4.5%, D3 group decreased by 48.8%, D4 group decreased by 2.2%, D5 group decreased by 8.5%, D6 group decreased by 45.4%, D7 group decreased by 48.8%, and D8 group decreased by 52.2%.

of rhinitis. The results showed that compared with the normal control group, the content of IL-4 in the model group increased significantly, and the content of IFN-gamma decreased relatively. After administration treatment, the level of INF gamma in the administration treatment group basically returned to the normal level, and the content of IL-4 was still significantly different from that in the control group ($p<0.05$).

TXB2 and TLB4 are substances released into tissues after allergic reaction. When allergic rhinitis occurs, TXB2 and TLB4 are produced by nasal mucosa stimulated by antigen, which then cause the corresponding symptoms of allergic rhinitis, especially nasal congestion and water clear runny nose. They are important transmitters mediating the symptoms of allergic rhinitis. The test results showed that the contents of TXB2 and TLB4 in nasal lavage solution in all model groups were significantly higher than those in the normal control group, which was consistent with the symptoms of sneezing and runny nose in the model construction group. After administration intervention treatment, there was no significant difference between D8 group, D7 group

TABLE 8

| Test results of final plasma cytokines of guinea pigs in each group | | | | | | |
|---|---|---|---|---|---|---|
| Group Index | IgE(ng/ml) | IL-4(pg/ml) | Histamine(ng/ml) | IFN-γ(pg/ml) | TXB2 (ng/ml) | LTB4 (ng/ml) |
| Normal | 11.19 ± 2.09 | 54.59 ± 6.42 | 13.92 ± 2.51 | 108.16 ± 13.11 | 14.21 ± 3.02 | 34.81 ± 3.85 |
| Placebo | 242.91 ± 27.6 | 636.93 ± 134.03 | 55.66 ± 2.35 | 22.2 ± 8.04 | 54.93 ± 3.48 | 86.99 ± 6.01 |
| D1 | 227.06 ± 24.85 | 549.03 ± 140.34 | 50.83 ± 4.06 | 29.99 ± 8.85 | 51.25 ± 5.74 | 83.59 ± 9.96 |
| D2 | 236.31 ± 32.69 | 581.77 ± 127.84 | 53.52 ± 2.57 | 26.82 ± 9.79 | 48.55 ± 3.47 | 81.89 ± 4.57 |
| D3 | 69.19 ± 15.45** | 259.94 ± 85.99** | 35.28 ± 4.82** | 92.3 ± 28.56** | 37.95 ± 5.11** | 42.22 ± 4.6** |
| D4 | 211.47 ± 19.73 | 592.15 ± 141.55 | 50.85 ± 5.15 | 29.85 ± 7.05 | 50.19 ± 5.37 | 83.34 ± 14.8 |
| D5 | 115.27 ± 20.848* | 431.8 ± 66.93* | 41.38 ± 5.41* | 38.27 ± 17.32 | 40.16 ± 4.86* | 52.03 ± 6.78* |
| D6 | 58.07 ± 16.56** | 230.08 ± 64.78** | 33.17 ± 7.46** | 85.64 ± 33.53* | 32.74 ± 7.17** | 32.75 ± 5.38** |
| D7 | 57.35 ± 13.18** | 210.08 ± 46.58** | 31.69 ± 3.47** | 94.77 ± 23.54** | 28.85 ± 3.14*** | 32.22 ± 6.45** |
| D8 | 41.86 ± 7.34 *** | 138.64 ± 39.91*** | 23.78 ± 3.86*** | 113.74 ± 12.59*** | 24.86 ± 4.5*** | 32.00 ± 6.71** |

(*$p < 0.05$, compared with placebo, **$p < 0.01$, compared with placebo)

IgE is the main antibody causing rhinitis. After allergen stimulation, the body produces IgE antibody, which can sensitize the body together with IgE receptor on the cell surface. Recontact with the same allergen will induce the release of inflammatory mediators. resulting in allergic reaction. The serum IgE content in the model group was significantly higher than that in the normal group ($p<0.01$). D8 group, D7 group, D6 group and D3 group could reduce the serum IgE content, which was significantly different from that in the model group ($p<0.05$).

INF-gamma and. IL-4 are important cytokines of Th1 and Th2 respectively, which play a core role in the pathogenesis and D6 group, which was slightly lower than that in D3 treatment group, and there was significant difference compared with the model control group ($p<0.05$). A: normal group, B: model group, C: D1 group, D: D2 group, E: D3 group, F: D4 group, G: D5 group, H: D6 group, I: D7 group, J: D8 group.

Figure 4:
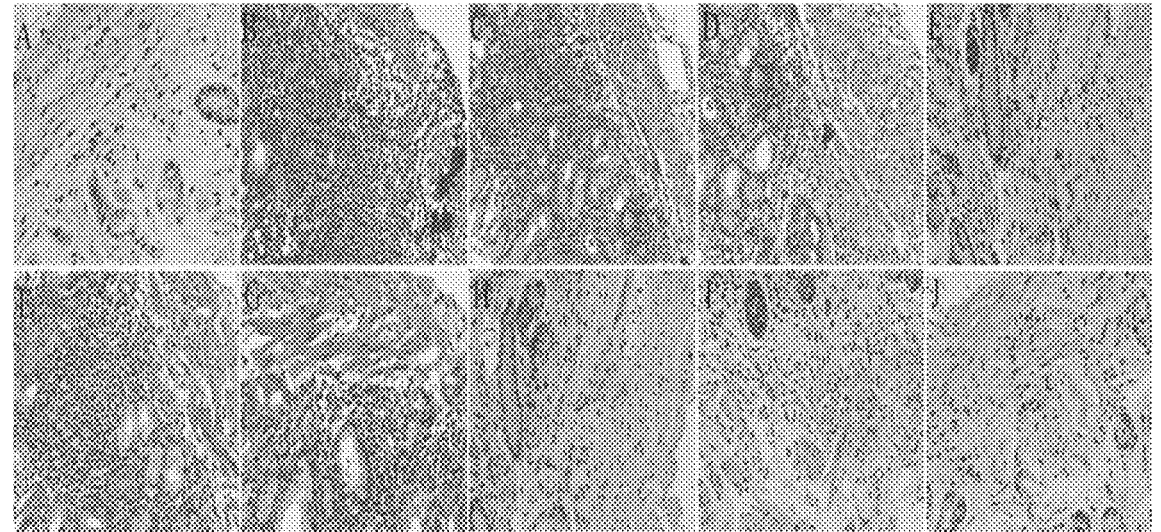
FIG. 4 shows the HE staining results of final nasal mucosa of guinea pigs in each group.

Finally, the nasal cavity and nasal septum mucosa of guinea pigs in each group were taken for tissue fixation and HE staining. The staining results of each group are shown in FIG. 4. The pathological analysis of each group is as follows:

In the normal group, the nasal mucosal epithelial cells of guinea pigs were structurally intact and columnar, no congestion and edema were found in glands and blood vessels, and a small number of inflammatory factors such as eosinophils were observed.

In the model group, the nasal mucosa of guinea pigs in the model group had a large number of eosinophils and lymphocytes infiltrating the upper cortex and lamina propria, edema of lamina propria, abscission of some mucosal epithelial cells and infiltration of intravascular inflammatory cells.

In D1 group, the nasal epithelial cells of guinea pigs were disordered in varying degrees, basement membrane was damaged and shed, glands proliferated, lamina propria blood vessels congested, tissue edema, accompanied by a large number of eosinophil infiltration.

In D2 group, there were a large number of eosinophils infiltrating the lamina propria of nasal mucosa, a large number of inflammatory granulocytes in blood vessels, edema of lamina propria and heavy shedding of mucosal epithelial cells in guinea pigs.

In D3 group, eosinophils and lymphocytes infiltrated into the epithelial layer and lamina propria in the nasal mucosa of guinea pigs. The edema of lamina propria was mild, the epithelial cells were complete, but the lamina propria was loose.

In D4 group, the nasal mucosa of guinea pigs had a large number of eosinophil infiltration, mainly between epithelial cells and lamina propria. There was no significant difference in inflammatory reaction between D4 group and the model group.

In D5 group, compared with the model group, the eosinophil and lymphocyte infiltration in the nasal mucosa of guinea pigs were reduced, the edema of mucosal lamina propria subsided, the epithelial cells fell off, and the tissue of mucosal lamina propria appeared loose.

In D6 group, the epithelial structure of nasal mucosa of guinea pigs was clear, the tissue was still slightly filled and edema, which was significantly reduced compared with the model group, the basement membrane structure had no significant change, and a small amount of lymphocyte infiltration could be seen.

In D7 group, a small number of eosinophils and lymphocytes infiltrated the epithelial layer and lamina propria, the edema of lamina propria was mild, the epithelial cells were complete and the blood vessels were clean.

In D8 group, the inflammatory reaction in nasal mucosa of guinea pigs was significantly reduced, mainly eosinophils and lymphocytes were significantly reduced, mucosal lamina propria edema was also significantly reduced compared with the model group, and mucosal epithelial cells were more complete.

Conclusion: from the above experimental results, it can be concluded that the composition of *Astragali radix, Atractylodes macrocephala* and *Schizonepetae herba* had a good effect on alleviating the symptoms of allergic rhinitis in guinea pigs.

Experiment 2 Mouse Immunity Enhancement Experiment

1) Experimental Animal 48 6-week-old clean mice, half male and half female, provided by Qinglongshan animal breeding center, license No. SCXK. (SU) 2017-0001. The mice were fed with convention al pellet feed (Jiangsu synergy biology Co., Ltd.) and kept in clean animal room. 12 h/12 h light/dark cycle, free feeding and drinking, temperature 20-26° C., relative humidity 40-70%.

2) Experimental Steps

① Experimental Animal Grouping

48 BALB/c mice were divided into 8 cages, with 6 BALB/c mice in each group, half male and half female. After adaptive growth for 7 days without abnormalities, they were used for drug administration evaluation. During the whole experiment, the animals were looked after and treated in strict accordance with the animal ethics law.

② Administration Intervention

After adaptive growth, drugs were administered by gavage. The gavage concentration of BALB/c mice in each group is shown in the table below. Each BALB/c mouse was subjected to gavage once a day for 4 weeks, i.e. 28 days.

③ General Observation of BALB/c Mice

| Group | Label | Preset administration dosage | Concentration |
|---|---|---|---|
| Normal | Normal | / | / |
| Competitive products on the market 1 | D1 | 69 mg/kg | 5 mg/ml |
| Competitive products on the market 2 | D2 | 75 mg/kg | 5 mg/ml |
| Laboratory sample 1 | D3 | 195 mg/kg | 15 mg/ml |
| Compound of *Astragali Radix* and *Atractylodes Macrocephala* | D4 | 195 mg/kg | 15 mg/ml |
| Low dose of compound of *Astragali Radix, Atractylodes Macrocephala* and *Schizonepetae Herba* | D5 | 97 mg/kg | 10 mg/ml |
| Middle dose of compound of *Astragali Radix, Atractylodes Macrocephala* and *Schizonepetae Herba* | D6 | 195 mg/kg | 15 mg/ml |
| High dose of compound of *Astragali Radix, Atractylodes Macrocephala* and *Schizonepetae Herba* | D7 | 390 mg/kg | 30 mg/ml |

④ Determination of Lymphocyte Transformation in Mice Induced by ConA

During the whole administration process, the state, mortality and abnormalities of animals in each group after administration were observed, recorded and counted. The fasting weight of mice was measured once a week and the volume of gavage administration was adjusted.

1) After the observation period, the mice in each group were killed by eyeball extraction and bloodletting. The killed mice were soaked in 75% ethanol for 5 min. The mice were dissected under sterile conditions, and the spleens of the mice were taken out.

2) The spleens of mice were milled on a 100-mesh screen, washed with Hank's solution, collected splenocyte suspension, centrifuged at 1000 rpm for 5 min, and the supernatant was discarded.

3) 10 ml of red blood cell lysate was added, the splenocytes and splenocytes were mixed evenly and stood at 37° C. for 10 min. After the red blood cells are completely broken, it was centrifuged at 1000 r/min for 5 min, and the supernatant was discarded. The supernatant was used, and the splenocytes were mixed evenly with PBS buffer, centrifuged at 1000 r/min for 5 min, and the supernatant was discarded. This step was repeated for 2-3 times.

4) The cells were resuspended in RPMI1640 culture medium, counted by trypan blue staining, and the cell concentration was adjusted to $5 \times 106$ pieces/ml;

5) 100 μL splenocyte suspension was added to 96 well cell culture plate respectively, and RPMI1640 medium was used as background control group to culture in 37° C. and 5% $CO_2$ incubator.

6) After 30 min, cells in each group were stimulated with RPMI1640 medium and ConA with a final concentration of 5 μg/ml. The medium was background control group and cultured in 37° C. and 5% $CO_2$ incubator.

7) After 72 h, 20 μL of 5 ml/ml MTT solution was added to each well of the culture plate. After continuous culture for 4 h, it was centrifuged at 2500 r/min for 10 min, and the supernatant was discarded. 100 μl of DMSO was added to each well. After the crystal of formazan in each well was completely dissolved, the absorbance of each well was measured at the wavelength of 490 nm.

8) The results were expressed by stimulation index (SI), and the formula was as follows:

$$SI = \frac{\text{Absorbance of } ConA \text{ stimulation group} - \text{Absorbance of blank group}}{\text{Absorbance of no } ConA \text{ stimulation group} - \text{Absorbance of blank group}}$$

⑤ Lymphocyte Stimulation Test

1) After resuspending the splenocyte suspension in step 3.4, it was counted with trypan blue staining, and the cell concentration was adjusted to $5 \times 106$ pieces/ml.

2) 100 μL splenocyte suspension was added to 96 well cell culture plate respectively, and RPMI1640 medium was used as background control group to culture in 37° C. and 5% $CO_2$ incubator.

3) After 30 min, cells in each group were stimulated with RPMI1640 medium and ConA with a final concentration of 5 μg/ml. The medium was background control group and cultured in 37° C. and 5% $CO_2$ incubator.

4) After 24 h, the cell culture medium of each well was collected, centrifuged at 1500 rpm and 4° C. for 10 min, and the supernatant was collected for cytokine determination.

⑥ Test of the Expression Levels of Cytokines in Cell Culture Supernatant by ELISA The cell culture supernatant was used to determine the contents of IgG, IL-2 and IL-6. The determination steps were as follows:

1) taking out the ELISA kit from the refrigerator and balancing it at room temperature for 20 min;

2) setting up blank, standard and sample wells to be tested respectively, where the blank wells do not add samples and enzyme labeling reagents, and during sampling, adding samples to the bottom of enzyme labeling plate, gently shaking and mixing the liquid in the enzyme labeling wells;

3) after sealing the film with a film sealing plate, placing it in a 37° C. incubator for incubation for 30 min;

4) discarding the liquid in the wells, gently spin drying it, and adding 50 μL biotin labeled antibody working solution to each well, and incubating in a 37° C. incubator for 30 min;

5) carefully removing the sealing film, pouring out the liquid in the wells, gently spin drying it, adding washing liquid into each well, standing at room temperature for 30 seconds and then pouring it out, repeating this operation for 5 times and gently patting it dry;

6) adding 50 μL horseradish peroxidase labeled avidin working solution to each well, and incubating in a 37° C. incubator for 30 min;

7) pouring out the liquid in the wells, gently spin drying it, adding washing liquid into each well, standing at room temperature for 30 seconds and then pouring it out, repeating this operation for 5 times and gently patting it dry;

8) adding 100 L color developing solution to each well in turn, and developing color in a 37° C. incubator without light for 15 min; and 9) adding 50 L termination solution to each well to terminate the reaction, then zeroing the blank wells and measure the absorbance (OD value) of each well at 450 nm wavelength, where the determination shall be carried out within 15 min after the termination solution is added.

⑦ Data Analysis

SPSS 22.0 statistical software was used for data analysis. The results in this evaluation process were expressed in the form of mean±standard error (x±SEM). Independent sample t-test was used for the comparison between the two groups, one-way ANOVA was used for the comparison of differences between multiple groups, the least significant difference method was used for pairwise comparison when the variance was homogeneous, and the rank sum test was used when the variance was uneven. $P < 0.05$ means significant difference, and $P < 0.01$ means extremely significant difference. Oligo 8.0 was used for mapping.

3. Experimental Results

1. Observation on the General State of BALB/c Mice in Each Group after Administration BALB/c mice did not die during the whole gavage period. See < batch record of mice immunity enhancement evaluation gavage administration > for body weight and dosage. During the whole administration period, diarrhea in mice occurred in D7 group, D3 group and D1 group during the first week of administration, and no intervention was given. The above phenomena did not occur at the beginning of the second week, and no other abnormal phenomena occurred at the end of intragastric administration and material collection.

2. Experimental Results of Splenocyte Proliferation Induced by ConA

Figure 5:
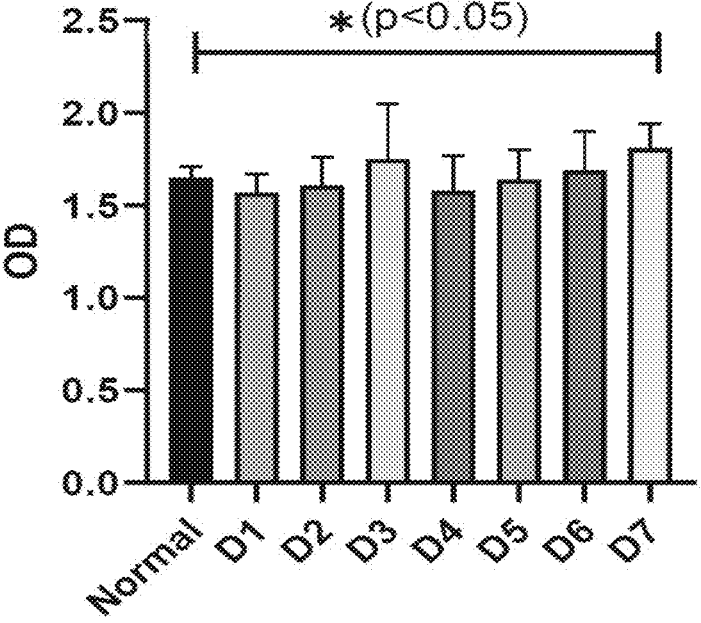
FIG. 5 shows the test results of ConA inducing splenocyte proliferation.
Figure 6:
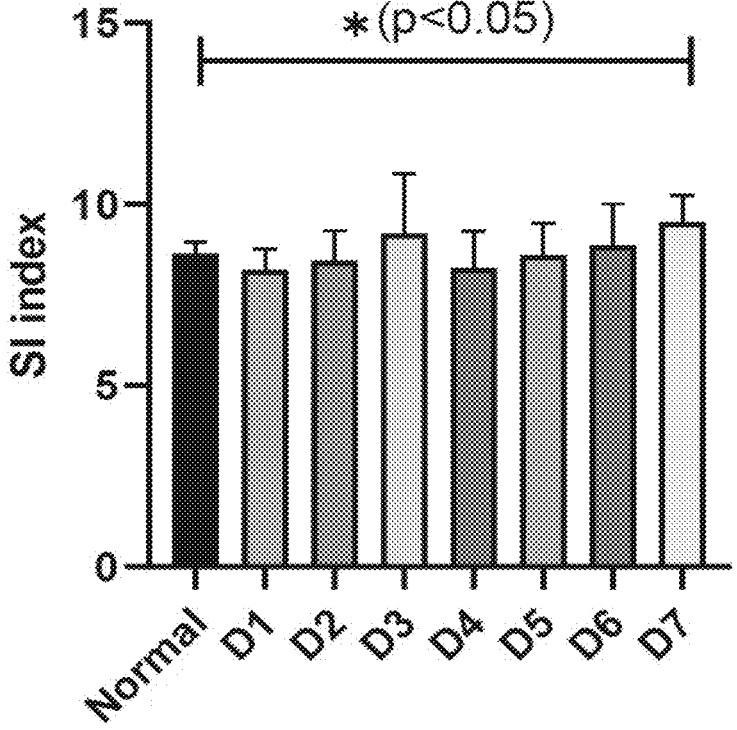
FIG. 6 shows the test results of ConA inducing splenocyte proliferation.

The test results of final splenocyte proliferation are shown in FIG. 5 and FIG. 6. In each group compared with the normal group, the OD value and stimulation index of cell proliferation of D3 group, D6 group and D7 group were slightly increased, but there was no significant difference between D3 group and D6 group ($p>0.05$), and D7 group was slightly higher, but the difference was significant ($p<0.05$). 4.3 determination results of cytokines of splenocytes induced by LPS.

3. Determination of Cytokines Splenocytes Induced by LPS

Figure 7:
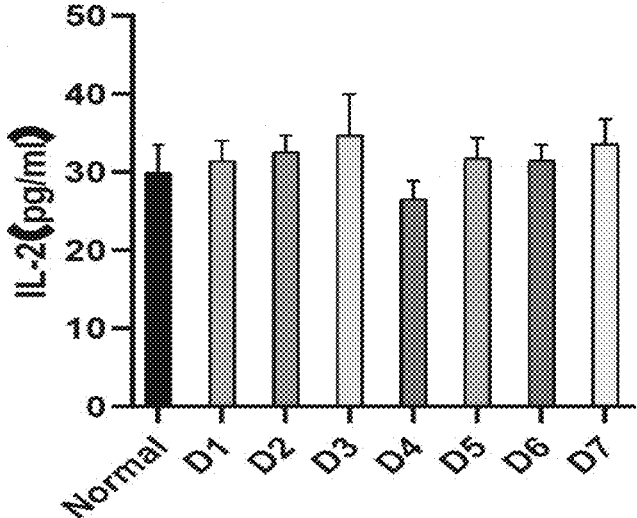
FIG. 7 shows the test results of LPS inducing IL-2 secretion of splenocytes.
Figure 8:
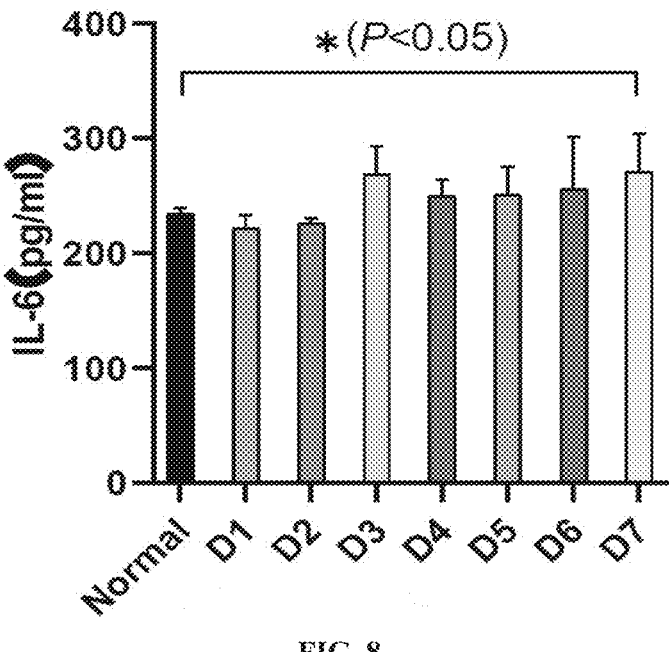
FIG. 8 shows the test results of LPS inducing IL-6 secretion of splenocytes.

The results of supernatant of final splenocytes induced by LPS are shown in FIG. 7. IL-2 secretion decreased slightly in D4 group and increased slightly in other groups, but there was no significant difference ($p>0.05$). The average secretion of IL-6 in D3 group, D4 group, D5 group, D6 group and D7 group was higher than that in the normal control group. In the results of significance analysis, there was no significant difference between D3 group and the control group ($p>0.05$), but increased compared with D7 group, and the difference was significant ($p<0.05$).

Figure 9:
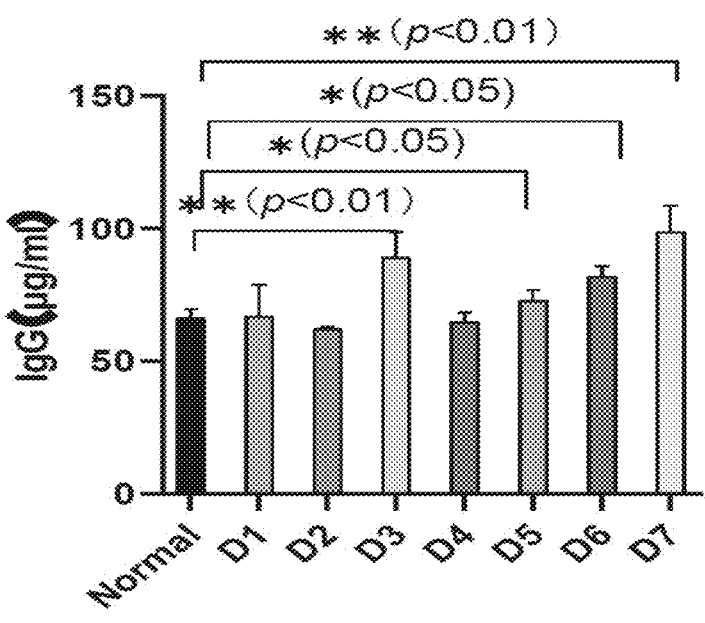
FIG. 9 shows the test results of LPS inducing IgG secretion of splenocytes.
Figure 10:
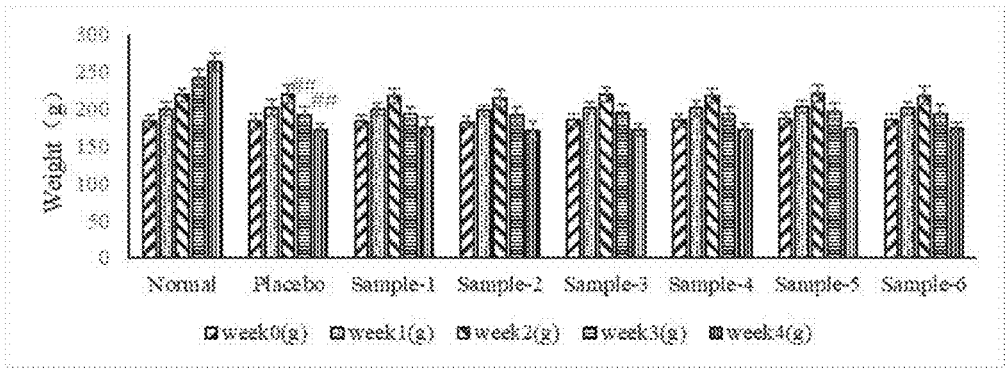
FIG. 10 shows the final weight measurement results of each group.
Figure 11:
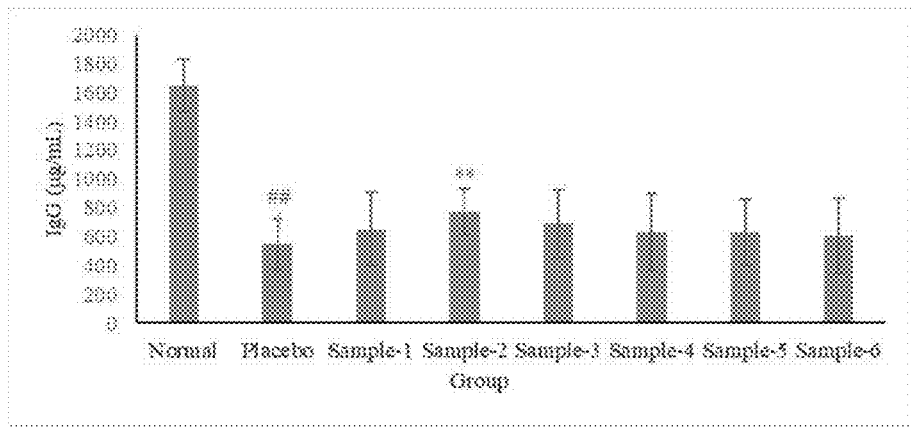
FIG. 11 shows the test results of serum IgG content.
Figure 12:
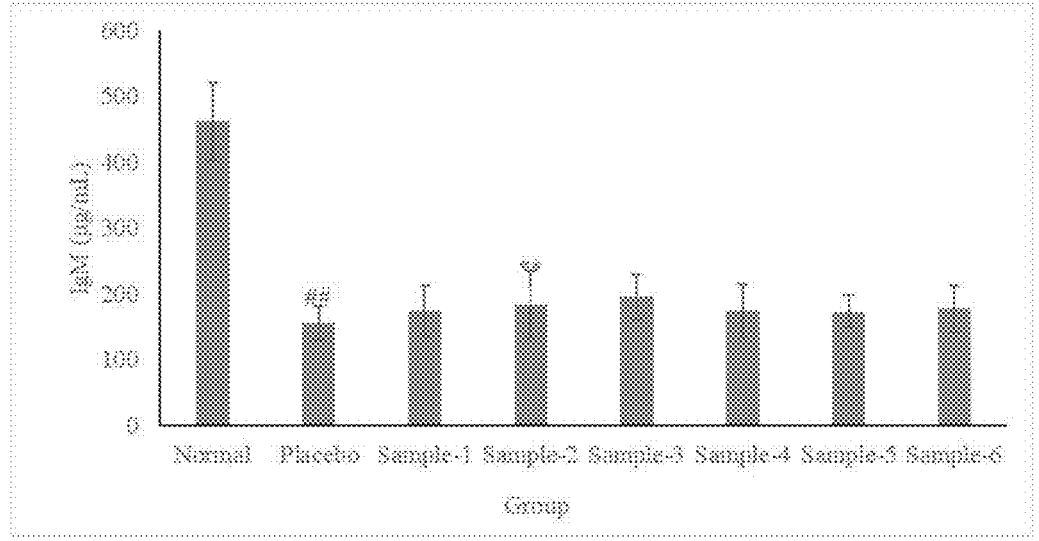
FIG. 12 shows the test results of serum IgM content.
Figure 13:
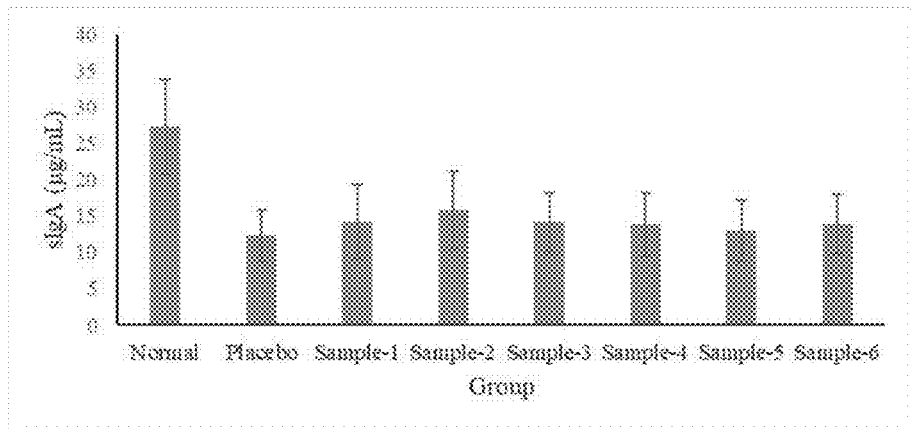
FIG. 13 shows the test results of saliva sIgA content.
Figure 14:
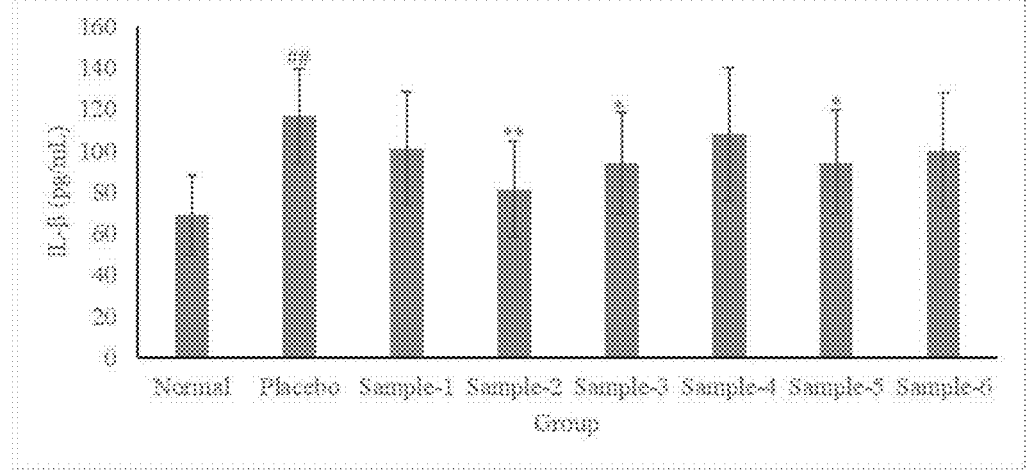
FIG. 14 shows the test results of serum IL-$\beta$ content.
Figure 15:
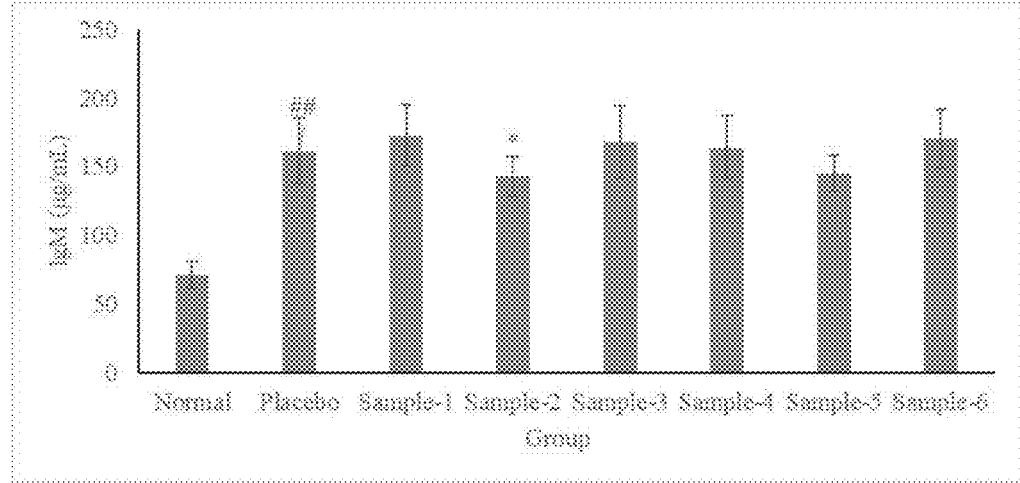
FIG. 15 shows the test results of serum IFN-$\gamma$ content.

The IgG results of splenocytes stimulated by LPS are shown in FIG. 9. The IgG content in the supernatant of D3 group, D5 group, D6 group and D7 group increased, and the difference was significant compared with the control group ($p>0.05$).

Experimental group: blank group, model group. *Atractylodes macrocephala* group, *Astragali radix* group, *Schizonepetae herba* group, low dose of compound group, middle dose of compound group, high dose of compound group, positive drug group.

Experimental Model 2: Cold Model of Immunocompromised Rats Induced by Cyclophosphamide

1. Experimental Animal 100 6-week-old clean rats, half male and half female, were provided by Qinglongshan animal breeding center, license No. SCXK, (SU) 2017-0001. The rats were fed with special pellet feed (Jiangsu synergy biology Co., Ltd.) and kept in clean animal room. 12 h/12 h light/dark cycle, free feeding and drinking, temperature 20-26° C., relative humidity 40-70%.

2. Experimental Steps

2.1 Experimental Animal Grouping

80 SD rats were divided into 20 cages, 5 SD rats in each cage, 2 cages in each group, 1 cage for male and female respectively. After 7 days of adaptive growth, 70 rats were used for drug administration evaluation and the construction of rat upper respiratory tract infection model, and the remaining 10 rats were used for normal control. During the whole experiment, the animals were looked after and treated in strict accordance with the animal ethics law.

2.2 Administration

After the adaptive growth, the drug was given by gavage once a day for each SD rat. The Placebo group and the normal control group were given the same volume of drug solution (i.e. normal saline) every day for 4 weeks, i.e. 28 days.

| Group | Label | Preset administration dosage | Concentration |
|---|---|---|---|
| Normal | Normal | / | / |
| Model | Placebo | / | Equal solvent |
| Low dose of compound | Sample-1 | 150 mg/kg | 30 mg/mL |
| High dose of compound | Sample-2 | 75 mg/kg | 15 mg/mL |
| *Atractylodes Macrocephala* | Sample-3 | 150 mg/kg | 30 mg/mL |
| *Astragali Radix* | Sample-4 | 150 mg/kg | 30 mg/mL |
| *Schizonepetae Herba* | Sample-5 | 150 mg/kg | 30 mg/mL |
| VC | Sample-6 | 30 mg/kg | 30 mg/mL |

2.3 Construction of SD Rat Model of Upper Respiratory Tract Infection

According to the method described in the preparation and application of medical experimental animal model and the standard operating procedures for the construction of upper respiratory tract infection model in the model animal center, SD rats in the normal control group were given the same amount of blank solvent. The specific steps were as follows.

1) On the 14th day after gavage administration, rats in the model group were intraperitoneally injected with cyclophosphamide for 3 consecutive days and strengthened once on the 20th day to prepare the immunosuppressive model.

2) On the 21st day, after the rats were placed in a low temperature environment overnight (4° C.), the cold symptoms such as burnout, decreased food intake and increased nasal secretion were found, which was regarded as successful modeling.

3) During the period of normal administration, the administration was ended on the 28th day, and the rats were killed.

4) Rats were observed and fed freely.

2.4 General Observation of SD Rats

The body weight of rats was measured once a week. During the administration, the general conditions, behavioral characteristics and death status of rats in each group, such as appetite, hair color and body posture, were observed. Nasal secretion and body temperature were observed ever day.

2.5 Final Plasma Collection of SD Rats

1) On the second day after the last administration, the rats were anesthetized by intraperitoneal injection of 10% chloral hydrate with the anesthetic dosage of 0.35 ml/100 g;

2) The abdominal cavity was opened, and a 5 ml sterile syringe was inserted into the abdominal vein of the rats, and the venous blood was drawn:

3) The drawn venous blood was put into a heparin tube, mixed well, and left in a chromatography freezer at 4° C. overnight.

4) After centrifugation at 14000 rpm at 4° C. for 15 minutes, the supernatant was taken and stored at −80° C. for use.

2.6 Final Upper Respiratory Tract Saliva Collection

1) On the second day after the last administration, the rats were anesthetized by intraperitoneal injection of 10% chloral hydrate with the anesthetic dosage of 0.35 ml/100 g;

2) SD rats were fixed in the supine and low head position, sterile cotton swabs were inserted into the upper respiratory tract of rats, dipped in rat saliva, and immediately placed in precooled normal saline and stored at −80° C. for use.

2.7 Test of the Expression Levels of Cytokines in Serum and Saliva of SD Rats by ELISA The final serum was used for IL-1β, IL-6, IL-12, IFN-γ, IgG, IgM, and saliva was used for the determination of sIgA. The determination steps were as follows:

1) taking out the ELISA kit from the refrigerator and balancing it at room temperature for 20 min;

2) setting up blank, standard and sample wells to be tested respectively, where the blank wells do not add samples and enzyme labeling reagents, and during sampling, adding samples to the bottom of enzyme labeling plate, gently shaking and mixing the liquid in the enzyme labeling wells;

3) after sealing the film with a film sealing plate, placing it in a 37° C. incubator for incubation for 30 min;

4) discarding the liquid in the wells, gently drying it, and adding 50 μL biotin labeled antibody working solution to each well, and incubating in a 37° C. incubator for 30 min;

5) carefully removing the sealing film, pouring out the liquid in the wells, gently spin drying it, adding washing liquid into each well, standing at room temperature for 30 seconds and then pouring it out, repeating this operation for 5 times and gently patting it dry;

6) adding 50 μL horseradish peroxidase labeled avidin working solution to each well, and incubating in a 37° C. incubator for 30 min;

7) pouring out the liquid in the wells, gently spin drying it, adding washing liquid into each well, standing at room temperature for 30 seconds and then pouring it out, repeating this operation for 5 times and gently patting it dry; and 8) adding 100 L color developing solution to each well in turn, and developing color in a 37° C. incubator without light for 15 min;

9) adding 50 μL termination solution to each well to terminate the reaction, then zeroing the blank wells and measure the absorbance (OD value) of each well at 450 nm wavelength, where the determination shall be carried out within 15 min after the termination solution is added.

2.8 Tissue Sampling and Pathological Staining of SD Rats

1) On the second day after the last administration, the SD rats were anesthetized by intraperitoneal injection of 10% chloral hydrate with the anesthetic dosage of 0.35 ml/100 g.

2) The nasal mucosa, nasopharynx tonsil and soft palate tonsil were peeled.

3) The above tissues were carefully removed and fixed with 4% paraformaldehyde for HE staining.

4) All the HE stained pathological sections were observed under the light microscope.

2.9 Data Analysis

SPSS 22.0 statistical software was used for data analysis. The results in this evaluation process were expressed in the form of mean±standard error (x±SEM). Independent sample t-test was used for the comparison between the two groups, one-way ANOVA was used for the comparison of differences between multiple groups, the least significant difference method was used for pairwise comparison when the variance was homogeneous, and the rank sum test was used when the variance was uneven. $P<0.05$ means significant difference, and $P<0.01$ means extremely significant difference. Oligo 8.0 was used for mapping.

3. Experimental Results

3.1 Weight Measurement Results of Each Group

TABLE 9

| | week 0(g) | week 1(g) | week 2(g) | week 3(g) | week 4(g) |
|---|---|---|---|---|---|
| | Dynamic weight measurement results of each group | | | | |
| Normal | 183.38 ± 8.28 | 200.02 ± 9.09 | 218.36 ± 8.54 | 241.33 ± 11.24 | 261.94 ± 12.83 |
| Placebo | 183.22 ± 10.56 | 200.87 ± 11.5 | 219.47 ± 12.59 | 192.18 ± 10.96 | 171.57 ± 9.33 |
| Sample-1 | 183.87 ± 6.87 | 199.6 ± 7.76 | 217.04 ± 9.54 | 192.78 ± 10 | 175.72 ± 12.03 |
| Sample-2 | 181.91 ± 7.26 | 197.4 ± 6.97 | 214.76 ± 11.33 | 190.8 ± 11.99 | 170.87 ± 12.12 |
| Sample-3 | 185.45 ± 8.39 | 201.26 ± 8.6 | 218.87 ± 10.32 | 194.42 ± 11.09 | 172.18 ± 7.97 |
| Sample-4 | 184.53 ± 8.85 | 200.36 ± 11.02 | 217.72 ± 9.69 | 193.34 ± 9.09 | 171.34 ± 8.41 |
| Sample-5 | 186.66 ± 8.33 | 202.55 ± 7.57 | 220.34 ± 11.1 | 195.79 ± 12.34 | 173.35 ± 7.93 |
| Sample-6 | 184.61 ± 7.84 | 200.37 ± 8.23 | 217.99 ± 12.26 | 193.64 ± 12.51 | 173.58 ± 7.48 |

3.2 Temperature Measurement Results of Each Group

TABLE 10

| Time | Normal | Placebo | Sample-1 | Sample-2 | Sample-3 | Sample-4 | Sample-5 | Sample-6 |
|---|---|---|---|---|---|---|---|---|
| | Dynamic temperature measurement results of each group | | | | | | | |
| Day 15 | 36.72 ± 0.22 | 36.76 ± 0.36 | 37 ± 0.44 | 36.99 ± 0.29 | 36.86 ± 0.39 | 36.65 ± 0.32 | 36.87 ± 0.43 | 36.84 ± 0.22 |
| Day 16 | 36.75 ± 0.24 | 36.9 ± 0.43 | 36.86 ± 0.41 | 37.05 ± 0.32 | 36.91 ± 0.45 | 37.05 ± 0.34 | 36.96 ± 0.38 | 36.78 ± 0.48 |
| Day 17 | 36.81 ± 0.23 | 37.05 ± 0.37 | 36.97 ± 0.29 | 37.03 ± 0.36 | 36.67 ± 0.34 | 37.05 ± 0.31 | 37.07 ± 0.36 | 36.9 ± 0.33 |
| Day 18 | 36.81 ± 0.26 | 36.8 ± 0.26 | 36.86 ± 0.27 | 36.79 ± 0.27 | 36.66 ± 0.28 | 36.6 ± 0.21 | 36.61 ± 0.27 | 36.6 ± 0.19 |
| Day 19 | 36.71 ± 0.27 | 36.74 ± 0.27 | 36.7 ± 0.23 | 36.63 ± 0.27 | 36.7 ± 0.22 | 36.73 ± 0.21 | 36.68 ± 0.23 | 36.63 ± 0.28 |

TABLE 10-continued

| | | | | | Dynamic temperature measurement results of each group | | | |
|---|---|---|---|---|---|---|---|---|
| Time | Normal | Placebo | Sample-1 | Sample-2 | Sample-3 | Sample-4 | Sample-5 | Sample-6 |
| Day 20 | 36.68 ± 0.21 | 36.83 ± 0.22 | 36.76 ± 0.25 | 36.71 ± 0.22 | 36.53 ± 0.26 | 36.75 ± 0.23 | 36.71 ± 0.25 | 36.69 ± 0.22 |
| Day 21 | 36.64 ± 0.18 | 36.81 ± 0.24 | 36.57 ± 0.26 | 36.78 ± 0.23 | 36.81 ± 0.31 | 36.8 ± 0.25 | 36.69 ± 0.27 | 36.41 ± 0.3 |
| Day 22 | 36.76 ± 0.25 | 38.07 ± 0.69 | 38.09 ± 0.49 | 38.11 ± 0.46 | 37.72 ± 0.52 | 38.43 ± 0.45 | 37.91 ± 0.65 | 37.89 ± 0.53 |
| Day 23 | 36.86 ± 0.23 | 38.15 ± 0.6 | 38.25 ± 0.51 | 37.94 ± 0.68 | 37.88 ± 0.54 | 38.31 ± 0.52 | 37.94 ± 0.57 | 38.23 ± 0.64 |
| Day 24 | 36.79 ± 0.25 | 37.77 ± 0.53 | 38.21 ± 0.61 | 37.75 ± 0.43 | 37.84 ± 0.59 | 38.36 ± 0.65 | 38.02 ± 0.47 | 38.11 ± 0.56 |
| Day 25 | 36.74 ± 0.27 | 38.02 ± 0.6 | 37.95 ± 0.41 | 37.92 ± 0.44 | 37.59 ± 0.54 | 38 ± 0.53 | 37.93 ± 0.42 | 37.87 ± 0.4 |
| Day 26 | 36.7 ± 0.19 | 37.5 ± 0.35 | 37.58 ± 0.39 | 37.22 ± 0.42 | 37.05 ± 0.36** | 37.26 ± 0.34 | 37.2 ± 0.46 | 37.41 ± 0.4 |
| Day 27 | 36.68 ± 0.18 | 37.45 ± 0.41 | 37.5 ± 0.4 | 37.15 ± 0.36 | 37.14 ± 0.32* | 37.23 ± 0.39 | 37.06 ± 0.29* | 37.32 ± 0.28 |
| Day 28 | 36.67 ± 0.25 | 37.58 ± 0.3 | 37.51 ± 0.31 | 36.88 ± 0.17** | 37.26 ± 0.38* | 37.42 ± 0.38 | 37.35 ± 0.27 | 37.62 ± 0.31 |

*p < 0.05,

**p < 0.01, compared with placebo

3.3 Test Results of Final Cytokines in Each Group

3.3.1 Test Results of Serum IgG Content

TABLE 11

| | | Test results of serum IgG content | | |
|---|---|---|---|---|
| | Normal | Placebo | Sample-1 | Sample-2 |
| IgG(µg/ml) | 1650.1 ± 182.98 | 550.69 ± 177.33 | 653.23 ± 254.39 | 771.58 ± 160.46** |
| | Sample-3 | Sample-4 | Sample-5 | Sample-6 |
| IgG(µg/ml) | 689.75 ± 238.72 | 632.2 ± 269.31 | 633.67 ± 227.83 | 606.77 ± 259.06 |

3.3.2 Test Results of Serum IGM Content

TABLE 12

| | | | Test results of serum IgM content | | | | |
|---|---|---|---|---|---|---|---|
| | Normal | Placebo | Sample-1 | Sample-2 | Sample-3 | Sample-4 | Sample-5 | Sample-6 |
| IgM(µg/ml) | 461.07 ± 59.9 | 155.69 ± 25.47 | 174.21 ± 38.43 | 183.11 ± 50.76 | 195.79 ± 33.57** | 174.05 ± 41.33 | 172.9 ± 24.9 | 177.1 ± 35.59 |

3.3.3 Test Results of Saliva sIgA Content

TABLE 13

| | | | Test results of saliva sIgA content | | | | |
|---|---|---|---|---|---|---|---|
| | Normal | Placebo | Sample-1 | Sample-2 | Sample-3 | Sample-4 | Sample-5 | Sample-6 |
| sIgA(µg/ml) | 27.31 ± 6.56 | 12.32 ± 3.56 | 14.27 ± 5.04 | 15.8 ± 5.46 | 14.14 ± 4.08 | 13.86 ± 4.34 | 13.09 ± 4.13 | 13.9 ± 4.08 |

3.3.4 Test Results of Serum IL-β Content

TABLE 14

| | | | Test results of serum IL-β content | | | | |
|---|---|---|---|---|---|---|---|
| | Normal | Placebo | Sample-1 | Sample-2 | Sample-3 | Sample-4 | Sample-5 | Sample-6 |
| IL-β(pg/ml) | 68.76 ± 19.15 | 116.63 ± 22.95 | 100.99 ± 27.34 | 81.32 ± 23.17** | 94.04 ± 24.38* | 108.02 ± 32.04 | 94.27 ± 25.21* | 100.12 ± 27.51 |

3.3.5 Test Results of Serum IFN-γ Content

TABLE 14

| | | | | Test results of serum IFN-γ content | | | | |
|---|---|---|---|---|---|---|---|---|
| | Normal | Placebo | Sample-1 | Sample-2 | Sample-3 | Sample-4 | Sample-5 | Sample-6 |
| IFN-γ(pg/ml) | 70.98 ± 9.49 | 161.16 ± 24.30 | 172.51 ± 22.58 | 143.05 ± 14.14* | 167.77 ± 26.27 | 163.73 ± 23.37 | 145.07 ± 12.92* | 170.49 ± 21.44 |

4. Conclusion

The high dose of compound group and low dose of compound group had significant effects on improving the late fever symptoms of cold rats and increasing the levels of IgG and IgM in cold model rats, and the effect was better than that of *Astragali radix, Atractylodes macrocephala* and *Schizonepetae herba*. It had a significant effect on reducing IL-β and IFN-γ in cold model rats, and the efficacy was positively correlated with the dose. The effects were better than those of *Astragali radix, Atractylodes macrocephala* and *Schizonepetae herba*. In conclusion, the traditional Chinese medicine compound composition disclosed in the disclosure can alleviate the cold symptoms of cold rats and improve the body immunity of cold rats.

The above description of the disclosed embodiments enables the skilled in the art to achieve or use the disclosure. Multiple modifications to these embodiments will be apparent to those skilled in the art, and the general principles defined herein may be achieved in other embodiments without departing from the spirit or scope of the disclosure. The present disclosure will therefore not be restricted to these embodiments shown herein, but rather to comply with the broadest scope consistent with the principles and novel features disclosed herein.

What is claimed is:

1. A traditional Chinese medicine compound composition with immune bidirectional regulation effect, wherein the traditional Chinese medicine compound composition is prepared by compounding a volatile oil and an extract, wherein;
   (i) the volatile oil is obtained after heating and refluxing of *Schizonepetae herba* with purified water, which a volume ratio of the *Schizonepetae herba* to purified water is 1: (5-20);
   (ii) the extract is obtained by jointly extracted by *Schizonepetae herba* extract residue from step (i), *Astragali radix* and *Atractylodes macrocephala*, with purified water, which a volume ratio of purified water to a total volume of the *Schizonepetae herba* extract residue, the *Astragali radix* and the *Atractylodes macrocephala* is (6-8): 1; and
   (iii) the traditional Chinese medicine compound composition consists of:
   1-100 parts by weight of *Schizonepetae herba,*
   1-300 parts by weight of *Astragali radix*; and
   1-150 parts by weight of *Atractylodes macrocephala*.

2. The traditional Chinese medicine compound composition with immune bidirectional regulation effect of claim 1, wherein an optimal ratio of the *Schizonepetae herba*, the *Astragali radix*, and the *Atractylodes macrocephala* in the traditional Chinese medicine compound composition is (1-2): (3-5): (1-2).

3. A composition comprising the traditional Chinese medicine compound composition of claim 1, wherein the composition is in the form of a dietary supplement or health food.

4. The composition of claim 3, wherein the composition is in a dosage form selected from the group consisting of capsule, granule or tablet.

5. The traditional Chinese medicine compound composition with immune bidirectional regulation effect of claim 1, wherein the volatile oil is embedded by β-cyclodextrin to form an embedded volatile oil, the traditional Chinese medicine compound composition is prepared by compounding the embedded volatile oil and the extract, and the traditional Chinese medicine compound composition consists of:
   1-100 parts by weight of *Schizonepetae herba;*
   1-300 parts by weight of *Astragali radix*; and
   1-150 parts by weight of *Atractylodes macrocephala*.

6. A preparation method of the traditional Chinese medicine compound composition with immune bidirectional regulation effect of claim 1 or 2, comprising compounding a volatile oil obtained after heating and refluxing of *Schizonepetae herba* and an extract jointly extracted by *Schizonepetae herba* extract residue, *Astragali radix* and *Atractylodes macrocephala*; wherein the preparation method specifically comprises:
   (1) heating and refluxing of the *Schizonepetae herba* with purified water, then collecting the volatile oil of the *Schizonepetae herba* and embed it with β-cyclodextrin for standby;
   (2) mixing the *Schizonepetae herba* extract residue filtered in step (1) with the *Astragali radix* and the *Atractylodes macrocephala*, adding purified water to continue extraction to obtain filtrates, and then combining the filtrates to obtain a traditional Chinese medicine extract; and
   (3) mixing the volatile oil obtained in step (1) with the traditional Chinese medicine extract obtained in step (2) evenly to obtain a mixture, then taking a supernatant after concentrating and ethanol precipitating the mixture, and spray drying and sieving the supernatant to obtain the Chinese medicine compound composition with immune bidirectional regulation effect.

7. The preparation method of the traditional Chinese medicine compound composition with immune bidirectional regulation effect of claim 6, wherein in step (1), a volume ratio of the *Schizonepetae herba* to purified water is 1: (5-20), a number of heating and refluxing times of the *Schizonepetae herba* is 1-3 times, and an extraction time is 1-3 h.

8. The preparation method of the traditional Chinese medicine compound composition with immune bidirectional regulation effect of claim 6, wherein a volume ratio of purified water to a total volume of the *Schizonepetae herba* extract residue, the *Astragali radix* and the *Atractylodes macrocephala* is (6-8): 1, the *Schizonepetae herba* extract residue, the *Astragali radix* and the *Atractylodes macrocephala* are heated and refluxed twice, a first heating and refluxing time is 1-2 h, and a second heating and refluxing time is 0.5-1.5 h.

9. The preparation method of the traditional Chinese medicine compound composition with immune bidirectional regulation effect of claim 6, wherein in step (3), a concentration of the ethanol precipitating is 70%, a spray drying temperature is 150-250° C., and a sieving mesh is 60-80 mesh.

\* \* \* \* \*